United States Patent
Salmun et al.

(12)
(10) Patent No.: US 6,432,972 B2
(45) Date of Patent: Aug. 13, 2002

(54) TREATING ALLERGIC AND INFLAMMATORY CONDITIONS

(75) Inventors: Luis M. Salmun, Short Hills; Richard R. Lorber, Scotch Plains, both of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/777,109

(22) Filed: Feb. 5, 2001

Related U.S. Application Data

(60) Provisional application No. 60/180,091, filed on Feb. 3, 2000.

(51) Int. Cl.[7] .............................................. A61K 31/44
(52) U.S. Cl. ...................................................... 514/291
(58) Field of Search ......................................... 514/291

(56) References Cited

U.S. PATENT DOCUMENTS

| | | | |
|---|---|---|---|
| 4,659,716 A | * | 4/1987 | Villani et al. |
| 5,595,997 A | * | 1/1997 | Aberg et al. |
| 5,900,421 A | * | 5/1999 | Handley et al. |
| 6,114,346 A | | 9/2000 | Harris et al. ................. 514/290 |

FOREIGN PATENT DOCUMENTS

| | | | |
|---|---|---|---|
| WO | WO 96/20708 | | 7/1996 |
| WO | WO 98/06394 | | 2/1998 |
| WO | WO9932125 | * | 7/1999 |

OTHER PUBLICATIONS

Vignola, A.M., et al., "Inhibitory activity of loratadine and descarboethoxyloratadine on expression of ICAM–1 and HLA–DR by nasal epithelial cells", Allergy, 1995, vol. 50, pp. 200–203.

Segura, T., et. al., Canadian. Journal of Allergy & Clinical Immunology, 1999, vol. 4, pp. 318–330.

Salmun, L.M., et al., "Efficacy & Safety of desloratadne in seasonal allergic rhinitis", Journal of Allergy and Clinical Immunology, Jan. 2000, vol. 105, No. 1 (part 2) p. 1123, Abstract No. 1123.

* cited by examiner

*Primary Examiner*—William R. A. Jarvis
*Assistant Examiner*—Vickie Kim
(74) *Attorney, Agent, or Firm*—Thomas D. Hoffman

(57) ABSTRACT

A method of treating and/or preventing congestion associated with allergic and inflammatory conditions of the upper and lower airway passages in a human, by administering an amount of desloratadine effective for such treating and/or preventing.

17 Claims, No Drawings

TREATING ALLERGIC AND INFLAMMATORY CONDITIONS

This application claims benefits of provisional application No. 60/180,091, filed Feb. 3, 2000.

BACKGROUND OF THE INVENTION

This invention relates to the use of desloratadine for the preparation of a medicament for treating and/or preventing congestion associated with allergic and inflammatory conditions, such as allergic rhinitis.

Desloratadine, disclosed in U.S. Pat. No. 4,659,716, is a non-sedating antihistamine useful for treating allergic reactions in animals including humans. U.S. Pat. No. 5,695,997 discloses pharmaceutical compositions containing desloratadine and methods of using desloratadine for treating and preventing disease states, e.g., allergic rhinitis.

Nasal congestion/stuffiness is a chronic symptom in patents with allergic disorders such as allergic rhinitis. However, currently available antihistamines have not been effective in treating nasal congestion/stuffiness associated with allergic disorders. Congestion associated with allergic rhinitis has been treated by the administration of combination products containing an antihistamine and the decongestant pseudoephedrine. For example, the Claritin D12 and D24 commercial products are combinations of loratadine and pseudoephredrine and the "Allegra-D" commercial product is a combination of fexofenadine and pseudoephedrine. See, Physicians Desk Reference 2000.

However, the administration of pseudoephedrine may cause unwanted side effects. Side effects associated with pseudoephedrine include insomnia, dizziness, weakness, tremor or arrhythmia. These and other unwanted side effects may cause patients suffering from congestion associated with allergic disorders to avoid or discontinue treatment with pseudoephedrine-containing products.

There is a need for a clinically effective therapy to treat or prevent such congestion associated with allergic and inflammatory conditions of the airway passages in a human with a non-sedating antihistamine which does not provide the potential adverse side effects that may be experienced with products containing pseudoephedrine. That is, there is a need for a non-sedating antihistamine that provides decongestant effect to reduce the amount of, or eliminate the need for, an additional decongestant such as pseudoephedrine.

SUMMARY OF THE INVENTION

The present invention provides a method of treating and/or preventing congestion associated with allergic and inflammatory conditions of the airway passages in a human, which comprises administering an amount of desloratadine effective for such treating and/or preventing. The present invention also provides a method of treating and/or preventing congestion associated with seasonal or perennial allergic rhinitis in a human which comprises administering an amount of desloratadine effective for such treating and/or preventing. The present invention further provides a method of treating and/or preventing congestion associated with allergic and inflammatory condition comprising administering desloratadine in combination with a reduced amount of one or more supplemental decongestants, such as pseudoephedrine.

DETAILED DESCRIPTION OF INVENTION

The phrase "allergic and inflammatory conditions of the airway passages" means those allergic and inflammatory conditions and symptoms found and in the upper and lower airway passages from the nose to the lungs. Typical allergic and inflammatory conditions or upper and lower airway passages include seasonal and perennial allergic rhinitis, non-allergic rhinitis, asthma including allergic and non-allergic asthma, sinusitis, and colds.

The term "congestion" means obstruction, stuffiness or blockage of the upper and/or lower airway passages from the nose to the lungs, including nasal congestion.

The amount of desloratadine effective for treating or preventing congestion associated with allergic and inflammatory conditions of the airway passages will vary with the age, sex, body weight and severity of the allergic and inflammatory condition of the patient. Typically, the amount of desloratadine effective for treating or preventing such allergic and inflammatory conditions is in the range of about 2.5 mg/day to about 45 mg/day, preferably about 2.5 mg/day to about 20 mg/day, or about 5.0 mg/day to about 15 mg/day, or about 5.0 mg/day to about 10 mg/day, more preferably about 5.0 mg/day to about 7.5 mg/day, and most preferably about 5.0 mg/day in single or divided doses, or a single dose of 5.0 mg/day.

U.S. Pat. No. 4,659,716 discloses methods of making desloratadine, pharmaceutical compositions containing it and methods of using desloratadine and pharmaceutical compositions containing it to treat allergic reaction in mammals. U.S. Pat. No. 5,595,997 discloses pharmaceutical compositions containing desloratadine and methods of using desloratadine for treating and preventing various disease states, e.g., allergic rhinitis. Desloratadine is available from Schering Corporation, Kenilworth, N.J.

The pharmaceutical compositions of desloratadine can be adapted for any mode of administration e.g., for oral, parenteral, e.g., subcutaneous ("SC"), intramuscular ("IM"), intravenous ("IV") and intraperitoneal ("IP"), topical or vaginal administration or by inhalation (orally or intranasally). Preferably desloratadine is administered orally.

Such pharmaceutical compositions may be formulated by combining desloratadine or an equivalent amount of a pharmaceutically acceptable salt thereof with a suitable, inert, pharmaceutically acceptable carrier or diluent that may be either solid or liquid. Desloratadine may be converted into the pharmaceutically acceptable acid addition salts by admixing it with an equivalent amount of a pharmaceutically acceptable acid. Typically suitable pharmaceutically acceptable acids include the mineral acids, e.g., $HNO_3$, $H_2SO_4$, $H_3PO_4$, HCl, HBr, organic acids, including, but not limited to, acetic, trifluoroacetic, propionic, lactic, maleic, succinic, tartaric, glucuronic and citric acids as well as alkyl or arylsulfonic acids, such as p-toluenesulfonic acid, 2-naphthalenesulfonic acid, or methanesulfonic acid. The preferred pharmaceutically acceptable salts are trifluoroacetate, tosylate, mesylate, and chloride. Desloratadine is more stable as the free base than as an acid addition salt and the use of the desloratadine free base in pharmaceutical compositions of the present invention is more preferred.

Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection. Solid form preparations may be converted into liquid preparations shortly before use for either oral or administration. Parenteral forms to be injected intravenously, intramuscularly or subcutaneously are usually in the form of sterile solutions and may contain tonicity agents (salts or glucose), and buffers. Opacifiers may be included in oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

In addition, the present invention includes combinations of desloratadine and other decongestants. Due to the decongestant effect of desloratadine, the other decongestants may be present in a reduced amount compared to other combinations of antihistamines and decongestants. Other decongestants which may be used in combination with desloratadine include pseudoephedrine, phenylephrine and phenylpropanolamine.

Preferably, the pharmaceutical preparation is in a unit dosage form. In such form, the preparation is subdivided into suitably sized unit doses containing appropriate quantities of the active component, e.g., an effective amount to achieve the desired purpose.

Desloratadine is particularly useful for the treatment and prevention of the nasal (stuffiness/congestion, rhinorrhea, nasal itching, sneezing) and non-nasal (itchy/burning eyes, tearing/watery eyes, redness of the eyes, itching of the ears/palate) symptoms of seasonal allergic rhinitis, including nasal congestion, in patients in need of such treating and/or preventing.

The clinical efficacy and safety of desloratadine has been documented in over 3,200 seasonal allergic rhinitis patients in four double-blinded, randomized clinical trials. The results of these clinical studies demonstrated the efficacy of desloratadine in the treatment of adult and adolescent patients with seasonal rhinitis.

Efficacy endpoints in all the studies were Total Symptom Score, Total Nasal Symptom Score, Total Non-nasal Symptom Score, and Health Quality of Life (HQOL) analysis in efficacy trials. Desloratadine (5 mg once daily) significantly reduced the total symptom scores (the sum of individual scores for rhinorrhea, sneezing, congestion/stuffiness, nasal itching, itchy/burning eyes, tearing, ocular redness, and itchy ears/palate). Desloratadine (5 mg) was significantly ($p<0.01$) more effective than placebo in reducing nasal symptoms. An important efficacy endpoint analyzed in the desloratadine studies is the AM NOW total symptom score. This parameter measures the total symptom relief by the patient after 24 hours before taking the next day dose. Statistically significant ($p<0.05$) reductions were maintained for the full 24 hour dosing interval over the entire 5 mg to 20 mg dosage range.

EXAMPLE

The effects of desloratadine on nasal congestion/stuffiness are described by using data pooled from randomized, parallel-group, double-blind, placebo-controlled studies of desloratadine in patients with SAR. Patients (12–75 years; pooled n-659–662/group) with a $\geq$2-year history of seasonal allergic rhinitis and moderate-to-severe symptoms present at the time of enrollment received desloratadine (5 mg or 7.5 mg) or placebo PO once a day for 14 days. The severity (0=none, 1=mild, 2=moderate, 3=severe) of congestion/stuffiness was assessed by patients for the study duration. The 14-day average change in symptom severity score from baseline was assessed. The mean symptom severity score for nasal congestion/stuffiness was 2.4 in each treatment group at baseline, indicating patients had moderate-to-severe nasal congestion before receiving treatment. Desloratadine significantly decreased nasal congestion/stuffiness (P=0.02 and 0.01 for 5 mg and 7.5 mg. respectively, of desloratadine vs placebo) as well as total symptom severity.

These data indicate that desloratadine, unlike other antihistamines, has the added benefit of providing significant relief from persistent allergic symptoms such as nasal congestion/ stuffiness in patients with SAR.

What is claimed is:

1. A method of treating or preventing congestion associated with allergic and inflammatory conditions of the airway passages in a human in need thereof which consists essentially of administering a therapeutically effective mount of desloratadine.

2. The method of claim 1 wherein the amount of desloratadine is about 2.5 mg/day to about 45 mg/day.

3. The method of claim 1 wherein the amount of desloratadine is about 5 mg/day to about 15 mg/day.

4. The method of claim 1 wherein the amount of desloratadine is about 5 mg/day to about 10 mg/day.

5. The method of claim 1 wherein the allergic reaction is seasonal allergic rhinitis, perennial allergic rhinitis, sinusitis, or allergic asthma.

6. A method of treating or preventing congestion associated with seasonal allergic rhinitis in a human in need thereof which consists essentially of administering a therapeutically effective amount of desloratadine.

7. The method of claim 6 wherein the amount of desloratadine is in the range of about 2.5 mg/day to about 45 mg/day.

8. The method of claim 6 wherein the amount of desloratadine is about 5 mg/day to about 15 mg/day.

9. The method of claim 6 wherein the amount of desloratadine is about 5 mg/day to about 10 mg/day.

10. A method of treating or preventing congestion associated with perennial allergic rhinitis in a human in need thereof which consists essentially of administering a therapeutically effective amount of desloratadine effective for such and/or preventing.

11. The method of claim 10 wherein the amount of desloratadine is in the range of about 2.5 mg/day to about 45 mg/day.

12. The method of claim 10 wherein the amount of desloratadine is about 5 mg/day to about 15 mg/day.

13. The method of claim 10 wherein the amount of desloratadine is about 5 mg/day to about 10 mg/day.

14. method of treating or preventing congestion associated with allergic asthma in a human in need thereof which consists essentially of administering a therapeutically effective amount of desloratadine.

15. The method of claim 14 wherein the amount of desloratadine is in the range of about 2.5 mg/day to about 45 mg/day.

16. The method of claim 14 wherein the amount of desloratadine is about 5 mg/day to about 15 mg/day.

17. The method of claim 14 wherein the amount of desloratadine is about 5 mg/day to about 10 mg/day.

* * * * *